(12) United States Patent
De Urbina Gaviria et al.

(10) Patent No.: US 10,941,432 B1
(45) Date of Patent: Mar. 9, 2021

(54) METHOD FOR THE PREPARATION OF LOW MOLECULAR WEIGHT PORCINE LYMPHO-RETICULAR POLYPEPTIDES

(71) Applicants: Santiago De Urbina Gaviria, Bogota (CO); Santiago De Urbina, Miami, FL (US)

(72) Inventors: Santiago De Urbina Gaviria, Bogota (CO); Santiago De Urbina, Miami, FL (US)

( * ) Notice: Subject to any disclaimer, the term of this patent is extended or adjusted under 35 U.S.C. 154(b) by 19 days.

(21) Appl. No.: 16/541,158

(22) Filed: Aug. 15, 2019

(51) Int. Cl.
  *C12P 21/06* (2006.01)
  *C07K 14/47* (2006.01)

(52) U.S. Cl.
  CPC .............. *C12P 21/06* (2013.01); *C07K 14/47* (2013.01)

(58) Field of Classification Search
  None
  See application file for complete search history.

(56) References Cited

U.S. PATENT DOCUMENTS

| | | |
|---|---|---|
| 4,361,586 A | 11/1982 | Meinke |
| 5,607,840 A | 3/1997 | Gorp et al. |
| 2017/0313987 A1 | 11/2017 | Petcavich |

FOREIGN PATENT DOCUMENTS

| | | |
|---|---|---|
| CN | 1634987 A | 7/2005 |
| CN | 102093440 B | 4/2013 |
| CN | 103589770 B | 12/2015 |
| CN | 106520877 A | 3/2017 |
| DE | 3929090 A1 | 3/1991 |
| EP | 0320717 A2 | 6/1989 |
| EP | 0325986 A2 | 8/1989 |
| EP | 0566877 B1 | 11/2002 |
| WO | 2015031762 A1 | 3/2015 |

OTHER PUBLICATIONS

Han et al., Porcine Splenic Hydrolysate has Antioxidant Activity in vivo and in vitro, Korean J. Food Sci. An. vol. 34, pp. 325-332 (2014).
Yu et al, Antioxidant Properties of Porcine Liver Proteins Hydrolyzed Using Monascus Purpureus, Food Sci. Biotechnol 26(5):1217-1225 (2017).

*Primary Examiner* — Anand D Desai
(74) *Attorney, Agent, or Firm* — The Morales Law Firm; Joseph L. Morales

(57) ABSTRACT

A method for preparation of low molecular weight porcine lympho-reticular polypeptides. The method comprises the enzymatic hydrolysis of a source of protein, wherein the source of protein comprises a blend of porcine liver and porcine spleen, with an enzyme having proteolytic activity and an enzyme having amylase activity.

15 Claims, 4 Drawing Sheets

The contents of the capsule prove not to be cytotoxic at concentrations of 5 mg/mL and below.

METHOD FOR THE PREPARATION OF LOW MOLECULAR WEIGHT PORCINE LYMPHO-RETICULAR POLYPEPTIDES

FIELD OF THE INVENTION

The present invention relates to a method for the preparation of low molecular weight polypeptides. More particularly, the present invention is related to an enzymatic hydrolysis method to produce low molecular weight lympho-reticular polypeptides.

BACKGROUND OF THE INVENTION

Since ancient times, proteins of animal and vegetal origin have been used for nutritional and developmental purposes. In fact, diets with normal intake of proteins ensure better development and functioning of physiological functions and organic defenses. Broths with specific protein content, e.g., liver, spleen, bone marrow, and/or blood, have been used for centuries, and as recently as the nineteenth and twentieth centuries, in order to accelerate convalescence in patients affected by a wide variety of pathologies. At the beginning of the twentieth century, various collaborators in Argentina began to use extracts from healthy tissues that they called lysates, obtained from different tissues of the human body, for the treatment of diseases that resulted in nutrient deficiencies.

The experience of more than a century using extracts from healthy tissues has demonstrated the excellent acceptance of proteins of animal origin, such as cattle, goats, and pigs, in human beings and the recognizable benefits towards the overall recovery of a patient.

After World War II, cancer treatment in Europe and North America was still in its infancy. Both, chemotherapy with nitrogen mustards and treatments with radio-therapy were used. They were dangerous, unsafe and had the potential to produce severe deleterious effects for doctors and patients. At that time, certain protein compounds obtained from splenic cell fragments of pig origin were found to provide energy and nutrition to the patients to whom such compounds were administered. These substances, called CT compounds and later SP1 compounds, fostered a significant decrease of tumor cellular glycolysis and effectively reversed a series of carcinoma and sarcoma type injuries.

The capacity of the CT and SP1 compounds to stimulate the production of T-lymphocytes, peripheral mononuclear cells and the release of intrinsic gamma-interferon, has led to the classification of these compounds as immune-stabilizers, modulators of biological response mechanisms (BRMs) or acute phase reactants (APRs), which positively activate production of Natural Killer Cells (NKC).

Due to the above-mentioned properties, the CT and SP1 compounds have been shown to be beneficial in a wide variety of immune-compromised pathologies, such as, HIV, herpes I and 2, herpes zoster, hepatitis B, rheumatoid arthritis, Sjögren syndrome, and dysplastic and aplastic anemia of different etiology, etc.

CT and SP1 compounds were also introduced for use in active treatment of tumoral injuries. Later, with the systematic use of chemotherapy and radiation treatments, CT and SP1 have been used as adjuvant therapy in oncological processes of various kinds. Experimental and clinical use in Europe and recently in Asia has demonstrated that the CT and SP1 compounds elicit useful therapeutic effects and have provided a significant improvement in the parameters of body weight, pain sensation, improvement of the general state, quality of life and increased survival in cancer patients undergoing traditional therapies such as chemotherapy and radiotherapy.

Processes for extracting CT and SP1 kind compounds are usually carried out through enzymatic hydrolysis of proteins in acidic media. The final composition and, therefore, the use of the hydrolysates depends mainly on the protein source, the type of protease used, the hydrolysis conditions and the degree of hydrolysis reached in the reaction.

A single mammalian tissue is typically used as the raw material for the hydrolysis process. Chinese patent application CN1634987A, for example, discloses a method of preparing polypeptide extracts from the spleen tissue of a mammal, other than a human. The process includes removing fat from the mammalian tissue, freeze-thaw crushing, homogenizing, adjusting the pH, precipitation, heating, centrifugation, filtration and ultrafiltration in order to obtain spleen polypeptide extract.

Chinese patent CN102093440B discloses a method for obtaining pig brain protein hydrolysate and monosialoganglioside (GM1) from fresh pig brain through fractional extraction.

Chinese patent application CN106520877A discloses a method for preparing pig cerebral protein antioxidative peptide. The method comprises pretreatment of pig brain to obtain degreased cerebral protein powder, ultrasonic treatment of pig cerebral protein powder, enzymatic hydrolysis to extract crude pig brain polypeptide, ultrafiltration with the molecular cut off of 3-5 kDa, and purification through a DEAE-52 fiber resin layer.

U.S. Pat. No. 5,607,840 discloses a method for the preparation of protein hydrolysate from mammalian tissue having an endothelial or mucosal component, being essentially the only tissue present in substrate suspension. Said mucosa tissue is obtained from at least one of intestines, intestinal mucosa, intestinal skin, trachea tissue, lung tissue, and liver tissue and being derived from at least one of pigs, cattle and sheep.

Chinese patent CN103589770B discloses an industrial method for enzymatic hydrolysis of proteins, starting from porcine whole blood proteins as the raw materials, in order to obtain peptides and amino acids.

Other authors refer to protein sources different than mammalian tissues as the raw material for the hydrolysis process. European patent application EP0325986A2 discloses a method for hydrolysis of food grade proteins of vegetable origin, particularly soy protein isolates, through contact of an aqueous suspension of the protein with a combination of protease from fungus of the species *Aspergillus oryzae* and an enzymatic extract of porcine pancreas.

International patent application WO2015/031762A1 discloses different methods for recovery of lipids, sugars, and proteins from microbial biomass of certain microalgae by enzymatic digestion. The method comprises the steps of treating microalgae with enzymes to produce digested biomass.

U.S. Pat. No. 4,361,586 discloses a process for enzymatic hydrolysis of fish or fish by-products characterized by the utilization of vacuum conditions during the hydrolyzing phase of the process to selectively remove the odoriferous compounds.

Most authors cite the exclusive use of enzymes with proteolytic activity in order to hydrolyze the protein source. German patent application DE3929090A1 discloses a process to produce a defined protein hydrolysate by using an effective in the acid range proteolytic enzymes, such as pepsin or acid proteinase of *Aspergillus*.

US patent application US20170313987A1 discloses a method of manufacturing pancreas Islet of Langerhans (IOL) mimetics, were the obtained product is hydrolysable by trypsin, cellulase, dextranase, gelatinase, pepsin, pancreatin, papain, or bromelain.

European patent application EP0320717A2 discloses the use of an enzymatic system obtained by extracting germinated sorghum seeds, for the hydrolysis of protein material from plant and animal sources.

European patent EP0566877B1 relates to a method of enzymatic hydrolysis of proteins and an apparatus for carrying out the method. The method described in that application uses proteolytic enzymes selected from the group consisting of trypsin, chymotrypsin, pancreatin, bacterial proteases, fungal proteases, and mixtures thereof.

In summary, the references found in the state of the art use a specific source of protein due to the importance of having a specific source of protein in the final extract. In case of extracts obtained from mammalian tissues, the references use of a single mammalian organ as the source of protein for the process.

SUMMARY OF THE INVENTION

A method for preparation of low molecular weight porcine lympho-reticular polypeptides. The method comprises the enzymatic hydrolysis of a source of protein, wherein the source of protein comprises a blend of porcine liver and porcine spleen, with an enzyme having proteolytic activity and an enzyme having amylase activity.

The blend of porcine liver and spleen, is present at a ratio of about 2:8 to 8:2 respectively, preferably 4:6 to 6:4. In some embodiments, the enzyme having proteolytic activity is selected from the group consisting of pancreatin, papain, pepsin, or mixtures thereof. The enzyme having amylase activity is diastase in some embodiments. In one embodiment, The papain is used at an amount ranging from 0.5 to 2.0 ounces per eleven pounds of the blend of porcine liver and spleen. In other embodiments, the pepsin is used at an amount ranging from 1.5 to 3.5 ounces per eleven pounds of porcine glands. The pepsin may be provided in the form of anhydrous pepsin.

In some embodiments, the pancreatin is used at an amount ranging from 0.05 to 1.0 ounces per eleven pounds of fresh porcine glands. The diastase is used at an amount ranging from 0.1 to 1.5 ounces per eleven pounds of fresh porcine glands.

In some embodiments of the method further comprises a cleansing step in an aqueous surfactant solution containing benzalkonium chloride. The enzymatic hydrolysis has a pH range of between 4.5 to 5.5. The pH range is maintained through the use of a weak organic acid, such as citric acid. In some embodiments, the method includes a step of adding Methyl 4-hydroxybenzoate and Propyl 4-hydroxybenzoate to the enzymatic hydrolysis. In further embodiments, the enzymatic hydrolysis is carried out at a temperature of 35° C. and 55° C.

These and other objects, features and advantages of the present invention will become clearer when the drawings as well as the detailed description are taken into consideration.

BRIEF DESCRIPTION OF THE DRAWINGS

The method described herein can be better understood, without further limitation, in connection with the accompanying drawings in which.

DETAILED DESCRIPTION OF THE INVENTION

A method for the preparation of low molecular weight porcine lympho-reticular polypeptides is described herein.

Figure 1:
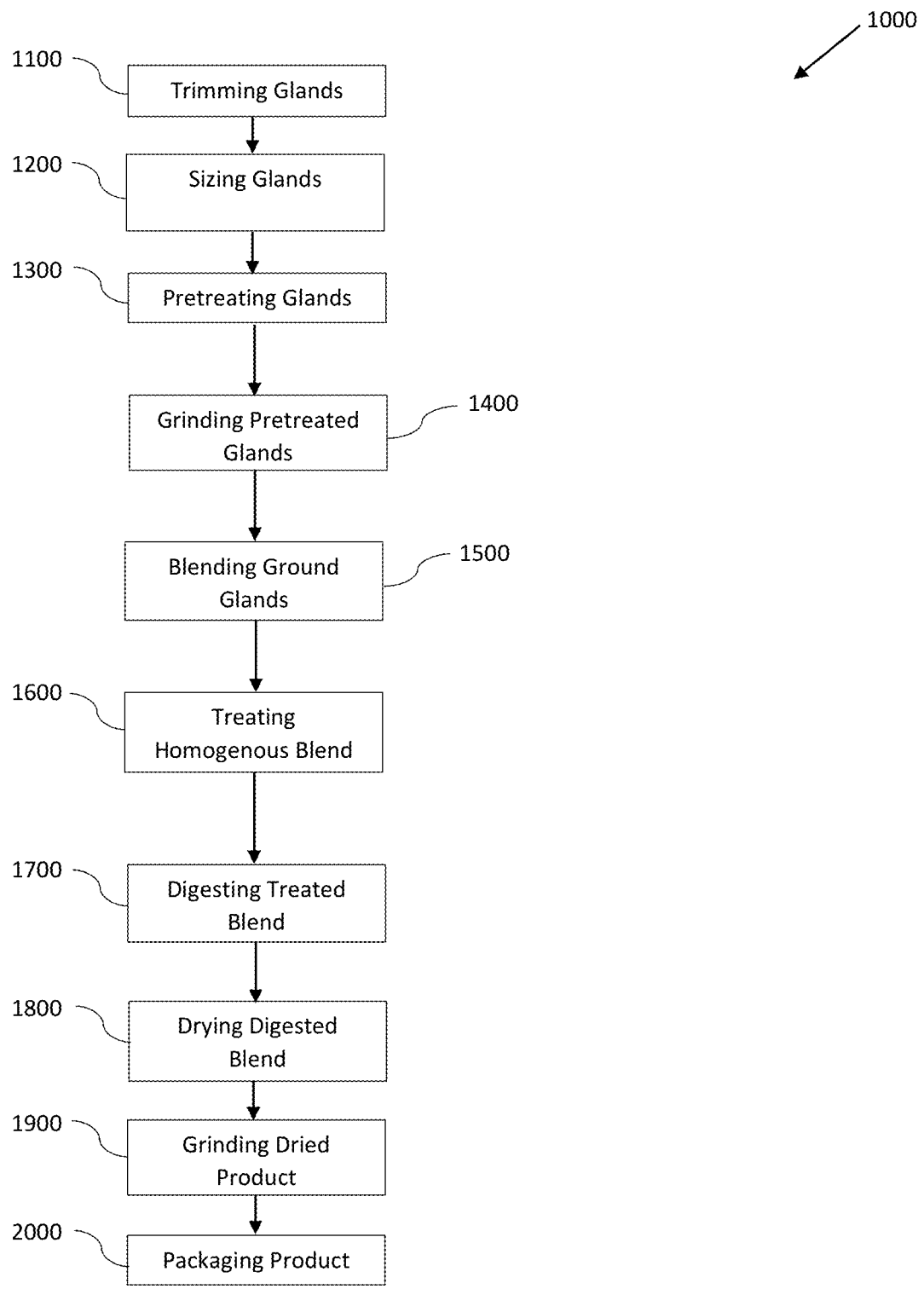
FIG. 1 is a diagrammatic representation of one illustrative embodiment of a method for the preparation of low molecular weight porcine lympho-reticular polypeptides.

FIG. 1 is a diagrammatic representation of one illustrative embodiment of a method 1000 for the preparation of low molecular weight porcine lympho-reticular polypeptides. The examples below are illustrative of a method 1000 for the preparation of low molecular weight porcine lympho-reticular polypeptides in accordance with at least one embodiment.

Turning to the illustrative embodiment of FIG. 1, the method 1000 for the preparation of low molecular weight porcine lympho-reticular polypeptides includes a trimming step 1100, which consists of trimming porcine glands to remove any fat and/or non-glandular tissue which may remain attached thereto. In at least one embodiment, porcine glands comprise a mixture of fresh porcine livers and fresh porcine spleens, and in still another embodiment, the porcine glands comprise about 60% by weight of fresh porcine livers and about 40% by weight of fresh porcine spleens. In some embodiments that ratio of liver to spleen ranges between 8:2 and 2:8, preferably between 6:4 and 4:6. In yet one further embodiment, an amount of about 6.6 pounds of fresh porcine livers and 4.4 pounds of fresh porcine spleens are utilized in the method 1000 for the preparation of low molecular weight porcine lympho-reticular polypeptides.

Liver and spleen were chosen as the source of protein because they are secondary organs of the immune system in mammalians, so they are expected to contain a high amount of proteins with activity over the immune system. On the other hand, porcine origin was chosen because it has been found a high degree of similarity between the human genome and the pig genome, which reduces the probability of allergic reactions, or other incompatibilities and adverse effects when the obtained polypeptides are administered as a dietary supplement for humans.

As described in more detail below, the glands are further sized 1200 to appropriate volume for further digestion of 1.5 to 27 cm$^3$ for liver and 0.625 to 1.0 cm$^3$ for spleen. The blended glands are then pretreated 1300 and the pretreated glands are further subjected to grinding 1400. The grinded glands are then blended 1500 to create a homogeneous blend. The treated homogeneous blend is then subject to digestion 1700. The digested blend is then dried 1800. The dried product is further grinded 1900 and packaged 2000.

Figure 2:
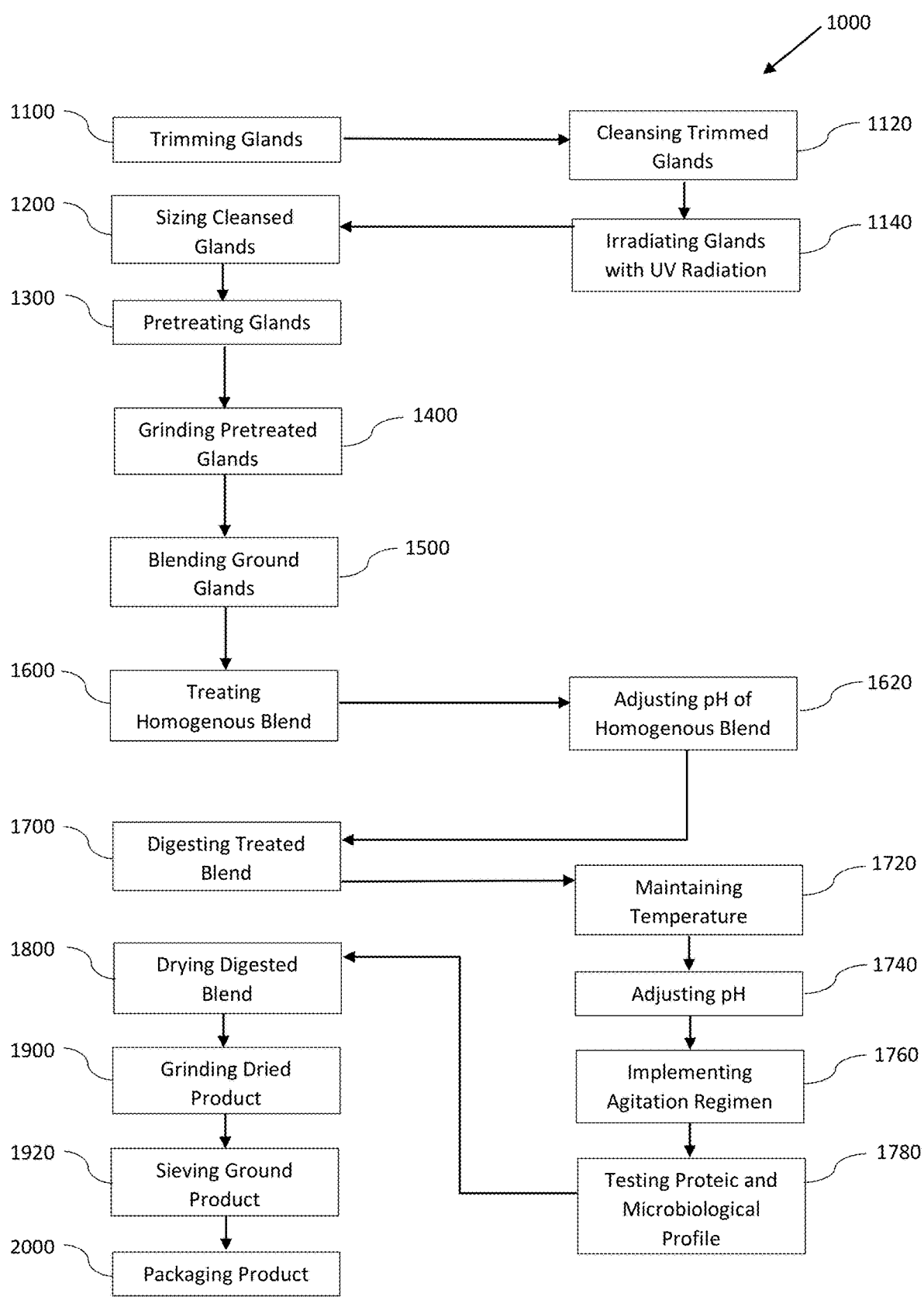
FIG. 2 is a diagrammatic representation of another illustrative embodiment of a method for the preparation of low molecular weight porcine lympho-reticular polypeptides.

As shown in FIG. 2, the present method 1000, in at least one embodiment, further comprises a cleansing step 1120 in which the trimmed porcine glands are cleaned. Trimmed porcine glands are cleansed in a dilute, i.e., 0.01% to 4.00% preferably 1.00% to 2.00% by weight, aqueous solution of a cationic surfactants, such as cetrimide, or other quaternary ammonium compounds, including benzalkonium chloride, benzethonium chloride, and other similar surfactants for a time of between 30 and 90 minutes, more preferably for about 60 minutes. Benzalkonium chloride is a surfactant which acts to burst the membrane of any germs which may be present in the trimmed porcine glands, thereby assuring germ free porcine glands for further processing.

In at least one further embodiment, an irradiating step 1140 is used in which the cleansed porcine glands are irradiated with ultraviolet radiation during storage and/or prior to further processing to assure germ free porcine glands for further processing.

The present method 1000 further comprises a sizing step 1200 for the trimmed/cleansed porcine glands, i.e., cutting the trimmed/cleansed porcine glands into small sized porcine glands pieces having a volume of 1.5 to 27 $cm^3$ for liver and 0.625 to 1.0 $cm^3$ for spleen. The glands can be cut in any shape appropriate for further processing. The glands can be cut into cubes, spheres, or any other type of shape.

The method 1000 further comprises a pretreating step 1300, wherein the sized porcine glands are pretreated with an enzyme which degrades proteins. In at least one embodiment, pretreatment step 1300 comprises soaking the sized porcine glands in an aqueous solution of papain. Papain is an enzyme that initiates the digestion of the porcine glands. In one embodiment, papain is added in a predetermined amount ranging from 0.5 to 2.0 ounces per eleven pounds of fresh porcine glands, in the form of an aqueous solution prepared by diluting about one ounce of papain in about seventeen fluid ounces of purified water. In at least one further embodiment, the sized porcine glands are soaked in an aqueous papain solution for a period of between 30 to 90 minutes, preferably for about 60 minutes.

The present method 1000 further comprises a grinding step 1400 in which pretreated porcine glands are grinded. In at least one embodiment, a stainless steel industrial grinder is employed to grind the pretreated porcine glands. In one embodiment, the grinding step 1400 includes grinding the pretreated porcine glands combined with the aqueous papain pretreatment solution.

The method 1000 for the preparation of low molecular weight porcine lympho-reticular polypeptides further comprises a blending step 1500 in which the ground porcine glands are blended until a homogenous blend is obtained. As with the grinding step 1400, a stainless steel industrial grade blender can be utilized in accordance with at least one embodiment for blending the ground porcine glands.

The present method 1000 further comprises a treating step 1600 in which the homogenous blend is treated with one or more digestive agents. The blend can be digested with either diastase, pepsin, or pancreatin, or any combination of such digestive enzymes. In at least one embodiment, the digesting step 1600 comprises mixing the homogeneous blend with a predetermined amount of digestive agents such as diastase, pepsin and/or pancreatin. In one embodiment, diastase is added in a predetermined amount ranging from 0.1 to 1.5 ounces per eleven pounds of fresh porcine glands; pepsin is added in a predetermined amount ranging from 1.5 to 3.5 ounces per eleven pounds of porcine glands; and pancreatin is added in a predetermined amount ranging from 0.05 to 1.0 ounces per eleven pounds of fresh porcine glands, in accordance with one embodiment of the present method 1000.

In yet one further embodiment, pepsin is provided in the form of anhydrous pepsin.

In at least one embodiment, the method 1000 comprises diluting the predetermined amounts of diastase, pepsin and/or pancreatin in an amount of purified water. The pH of the aqueous pepsin and pancreatin solution is adjusted 1620 to about 4.5 to about 5.5 before it is added to homogenous blend. A diluted solution of a weak organic acid, for example, citric acid in a range from 1.5 to 5.5 ounces per eleven pounds of fresh porcine glands, is utilized to adjust the pH of the aqueous diastase, pepsin and/or pancreatin solution.

The present method further comprises a step for preventing hydrolysis of the proteins and microbiological contamination. This step includes the addition of a mixture composed by Methyl 4-hydroxybenzoate and Propyl 4-hydroxybenzoate to the previous blend comprising the porcine glands used as the source of protein and the digestive agents used as the enzymatic system. Methyl 4-hydroxybenzoate is used in an amount ranging from 0.4 to 1.0 ounces per eleven pounds of fresh porcine glands and the Propyl 4-hydroxybenzoate is used in an amount ranging from 0.1 to 0.5 ounces per eleven pounds of fresh porcine glands.

The method 1000 for the preparation of low molecular weight porcine lympho-reticular polypeptides further comprises a second digesting step 1700, wherein the treated blend is transferred to a reactor, or digester, and allowing the digestive agents to digest the treated blend in a controlled digester environment.

In accordance with one embodiment, the digesting step 1700 is carried out at a predetermined temperature range 1720. In one embodiment, the predetermined temperature range is between 35° C. and 55° C., preferably between 40° C. and 50° C. In a preferred embodiment, a temperature range during the digesting step 1700 is between 43° C. and 47° C., and in one further embodiment, the predetermined temperature range of between 44° C. and 46° C.

In further embodiments, the pH of the treated blend in the digester is adjusted 1740 to a predetermined pH range. In one embodiment, the predetermined pH range of between 3.8 and 7.2, preferably between 4 and 7. In one further embodiment, the pH of the treated blend in the digester has a predetermined pH range of between 4.5 and 5.5. In still one further embodiment, the pH of the treated blend in the digester has a predetermined pH range of about 5.5 to about 6.0.

In one embodiment, digesting step 1700 further comprises agitation 1760 of the treated blend in the digester. In one embodiment, the agitation 1760 comprises an agitation period followed by a period of repose, and in one further embodiment, an agitation 1760 comprises a continuous repetitive cycle of an agitation period followed by a period of repose. In at least one embodiment, agitation 1760 of the treated blend in the digester comprises providing an agitation period of from 4 to 8 minutes, preferably about six minutes followed by a period of repose of from 2 to 6 minutes, preferably about four minutes. In yet one further embodiment, agitation 1760 of the treated blend in the digester comprises providing a continuous repetitive cycle of from 4 to 8 minutes, preferably a six minute agitation period, followed by a 2 to 6 minutes, preferably about four minute period of repose over a 22 to 26 hour, preferably a twenty-four hour period.

In at least one embodiment, the present method 1000 for preparing low molecular weight porcine lympho-reticular polypeptides comprises testing 1780 protein and microbiological profiles of samples of the treated blend obtained intermittently from the digester while digesting the treated blend in the digester. Such testing 1780 allows verification of the concentration of porcine lympho-reticular polypeptides present, as well as to verify that the treated blend has not been contaminated by microbes.

The present method 1000 for the preparation of low molecular weight porcine lympho-reticular polypeptides further comprises drying 1800 a digested blend. In at least one embodiment, drying 1800 the digested blend comprises spreading the digested blend in thin layers onto the drying trays which are then placed into a drying oven. In one embodiment, the drying oven comprises dry air injection to facilitate drying of the digested blend. In at least one embodiment, drying trays are constructed of stainless steel, and in one further embodiment, the drying trays comprise a plurality of drying apertures formed there through to facilitate passage of heated dry injection air through the digested blend to facilitate drying of the same. A temperature controller is employed in at least one embodiment to maintain the temperature in the drying oven in a range of between 35° C. and 55° C., preferably between 40° C. and 50° C. In at least one embodiment, drying the digested blend 1800 comprises maintaining the temperature in a drying oven at about 50° C. for about eight hours.

Once the digested blend has been dried, the present method 1000 comprises grinding 1900 the dried product. In at least one embodiment, grinding 1400 the dried product comprises placing the dried product into a stainless steel industrial grinder and rendering a fine homogenous powder. In at least one further embodiment, the present method 1000 comprises sieving 1920 the ground product through a sieve. The sieve may be constructed of stainless steel, and in at least one embodiment, comprises a sieve size in the range of between 20 and 40 (standard US measurement).

The present method 1000 for preparing low molecular weight porcine lympho-reticular polypeptides further comprises packaging 2000 a low molecular weight porcine lympho-reticular polypeptide product, wherein the sieved product is placed in opaque plastic bags and stored in an inert atmosphere, such as nitrogen. In at least one embodiment, the packaged product is maintained at a maximum storage temperature of about 30° C.

One exemplary embodiment disclosed herein is a low molecular weight porcine lymphoreticular polypeptides prepared in accordance with the method 1000 described herein.

Another product comprises a dried blend of porcine glands, namely liver and spleen, that have been processed in accordance with the method described herein.

With the foregoing understanding of the present method 1000, the following examples are illustrative of some non-limiting specific embodiments.

EXAMPLES

Example 1: Preparation of Low Molecular Weight Porcine Lympho-Reticular Polypeptides Ingredients/Reagents.

Fresh porcine liver (certified free of antibiotics and hormones). Fresh porcine spleen (certified free of antibiotics and hormones). Benzalkonium chloride solution (1-2% concentration). Purified water. Papain (diluted in the purified water). Pepsin (anhydrous). Pancreatin. Diastase. Citric acid. Methyl 4-hydroxybenzoate. Propyl 4-hydroxybenzoate.

Equipment.

Stainless steel meat grinder. Stainless steel industrial blender. Stainless steel digester with temperature, pH, and agitation controls. Drying oven with temperature and vacuum controls. Stainless steel drying trays. Stainless steel sieves. Scale. Laboratory glassware. pH meter/controller. Storage bags and containers Preparation.

Approximately 6.6 pounds of fresh porcine livers and 4.4 pounds of fresh porcine spleens, both certified to be free of antibiotics and hormones, are weighed out and trimmed to remove any fat or foreign matter. The trimmed porcine livers and spleens are cleansed for about one hour in a benzalkonium chloride solution having a concentration of about one to two percent, by weight.

Benzalkonium chloride is a surfactant which causes the membranes of any germs present in the porcine livers or spleens to burst, thereby assuring germ free raw materials for use in the present process. The trimmed porcine livers and spleens may be irradiated with ultraviolet light to further assure that the porcine glands are germ free.

The cleansed porcine livers and spleens are cut into small pieces and pretreated for about one hour in about seventeen ounces of purified water having about one ounce of papain previously diluted therein. The papain solution initiates the digestion process and softens the porcine livers and spleens to facilitate further processing.

The pretreated porcine glands are ground 1400 along with the papain solution utilizing a stainless steel industrial grinder, and the ground porcine glands are then blended 1500 together, once again, along with the papain solution, in a stainless steel industrial blender until a homogenous blend is obtained.

A stainless steel digester is preheated to a temperature of about 40° C., and the homogenous blend of the pretreated porcine glands is added thereto with an aqueous solution comprising about 0.5 ounces of diastase, about 2.1 ounces of anhydrous pepsin and about 0.1 ounces of pancreatin mixed therein. An amount of diluted citric acid is added as needed to adjust the pH of the aqueous pepsin and pancreatin solution to a range of about 5.5 to about 6.0. A temperature controller is programed to maintain the treated blend in the digester at a temperature of about 45° C. throughout the digestion process, which is about twenty-four hours.

A pH controller may be utilized, and diluted citric acid is added as needed throughout the digestions process to adjust the pH of the treated blend in the digester in a range of about 5.5 to 6.0.

0.5 ounces of Methyl 4-hydroxybenzoate and 0.2 ounces of Propyl 4-hydroxybenzoate are then added to the stainless steel digester containing the blend comprising the porcine glands and the enzymatic system.

An agitation regimen is implemented in the stainless steel digester and consists of about six minutes of agitation followed by about four minutes of repose. This agitation 1760 regimen is continuously repeated over the entire digestion process which, once again, is about twenty-four hours.

Samples are obtained periodically throughout the digestion process to verify the protein profile of the treated blend, as well as to conduct microbiological tests to assure that the treated blend has not been contaminated during the digestion 1700 step. In the event a pH controller is not employed, the pH of the periodic samples is measured and the pH of the treated blend is adjusted 1740 as may be needed by the addition of diluted citric acid.

After about twenty-four hours in the digester, the digested 1700 blend is spread onto stainless steel drying trays which are placed into a drying oven for drying 1800. The drying oven uses forced dry air and the drying trays have numerous apertures to permit the forced airflow therethrough to shorten the overall drying time required to about eight hours. A temperature controller maintains the temperature in the drying oven at about 50° C. The temperature controller is further programmed to assure that at no time does the over dryer temperature exceed 50° C., as protein degradation may occur at temperatures in excess of 50° C.

The dried product is placed into the stainless steel industrial grinder to form a fine homogenous powder, which is passed through a stainless steel sieve having sieve size in the range of 20 to 40 (standard US measurement). The sieved product is placed in opaque plastic bags and stored in an inert atmosphere, such as nitrogen, and is maintained at a maximum storage temperature of about 30° C.

Example 2: Evaluation of Cytotoxicity and Anti-Inflammatory Effects of Low Molecular Weight Porcine Lympho-Reticular Polypeptides The cytotoxicity and anti-Inflammatory effects of low molecular weight lympho-reticular polypeptides obtained in the Example 1 were evaluated in human cell cultures.

A Human Acute Monocytic Leukemia cell line—THP-1 was used for the purpose of this study. Cells were maintained in log phase growth in 75 cm2 Falcon cell culture flaks containing complete medium (CM):Gibco RPMI 1640-L-Glutamine medium supplemented with 10% fetal bovine serum and 100 U/mL Gibco Pen Strep. Cell cultures were incubated at 37° C. under 5% CO2 in a humidified atmosphere.

THP-1 cells were seeded in 96 well plates with 200 μL CM containing 5.0×105 cells and treated with 50 ng/mL PMA for 48 hours to induce differentiation into macrophage-like cells MDM, then washed 4× with CM and allowed to rest for 5 to 7 days with media exchanged for fresh media every two days. MDM were stimulated with 2 μg/mL LPS (E. coli serotype 055: B5 Ready-Made LPS solution 1 mg/mL, 0.2 μm filtered).

To test for cytotoxicity, the supernatant of the product partially dissolved in 5 mL of culture media were added to MDM (approx. 1×106 cells/well with 200 μL of CM) at concentrations 10 ng-200 mg in 96 well plates. After 24 hours of incubation, 20 μL of Cell titer 96 Aqueous One Solution MTS 5 mg/mL was added and incubated for an additional 4 hours. Dual absorbance readings were taken in an Epoch microplate reader at λ=490 nm and 650 nm.

Cytokines in culture supernatants fluids treated at product concentrations of 10 ng-200 mg were assayed using complete TNF-α capture antibody Novex ELISA kits according to manufacturers' instructions. Cytokine concentrations were determined within 30 min of the stop reaction. Dual absorbance readings were taken in an Epoch microplate reader at 450 nm and 650 nm respectively.

Statistical analysis was performed using a two-tailed t-test where indicated. p<0.05 was considered significant. Experiments and measurements were performed in duplicate.

Figure 3:
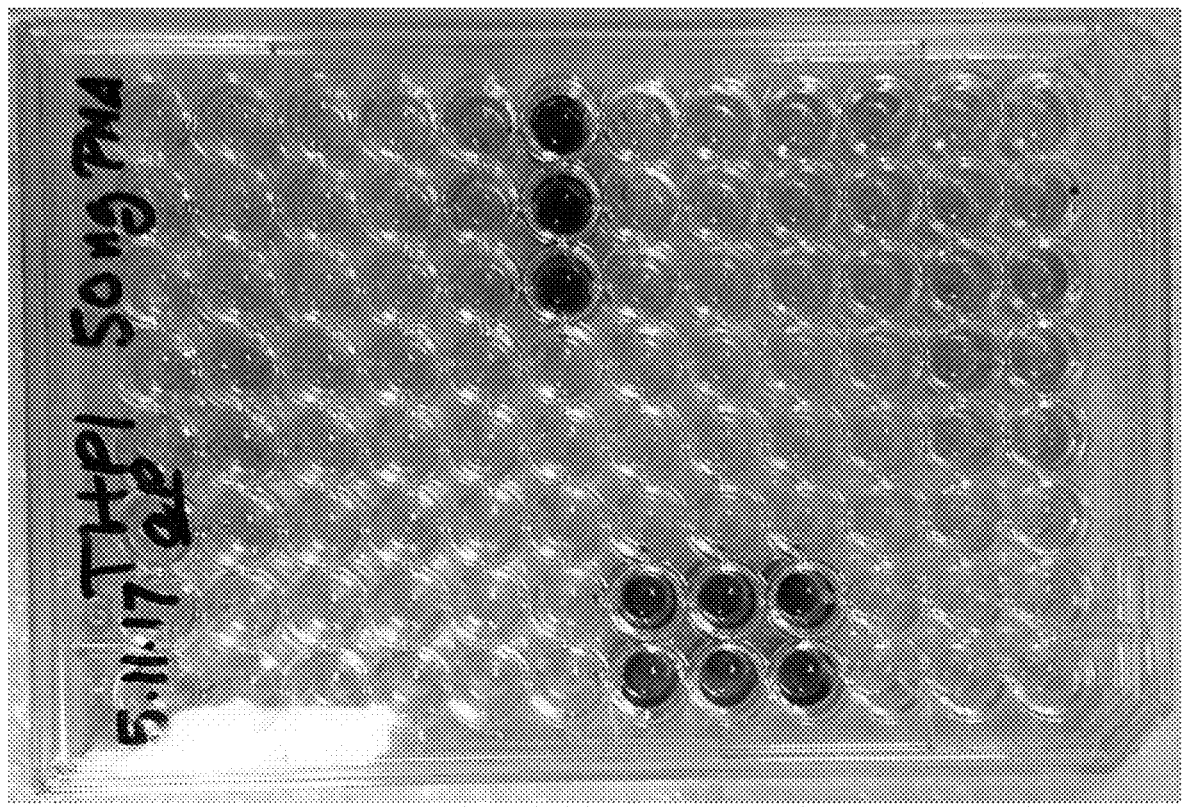
FIG. 3 shows the results of the cytotoxicity effect of the low molecular weight porcine lympho-reticular polypeptides. Absorbance measurements at $\lambda$=490 nm determined no differences in cell viability between the cells treated with the product at and below 5 mg/mL and the non-treated and LPS activated MDM, suggesting that the product is non-cytotoxic at the experimental concentrations of 5.0 mg/mL and below.
Figure 3:
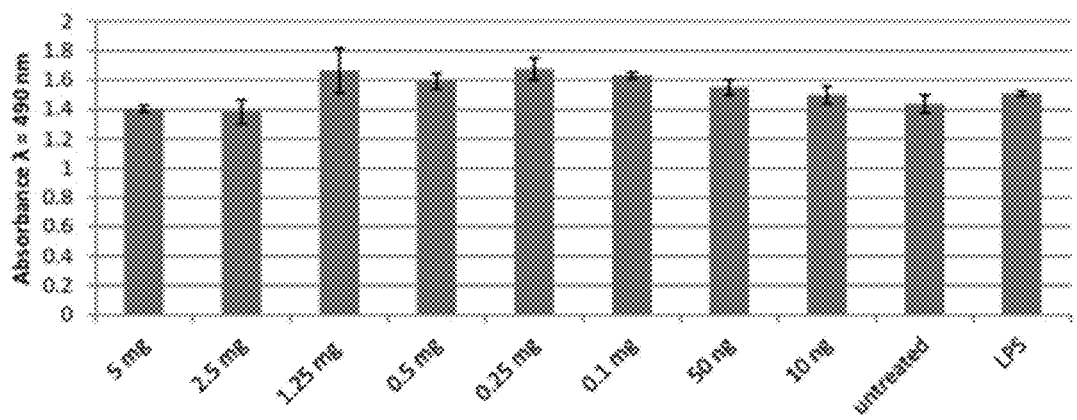

At concentrations of 10 mg/mL to 200 mg/mL, the product resulted cytotoxic to differentiated macrophage-like THP-1 cells, while at concentrations of 5 mg/mL to 10 ng, the product proved non-cytotoxicity. FIG. 3.

Figure 4:
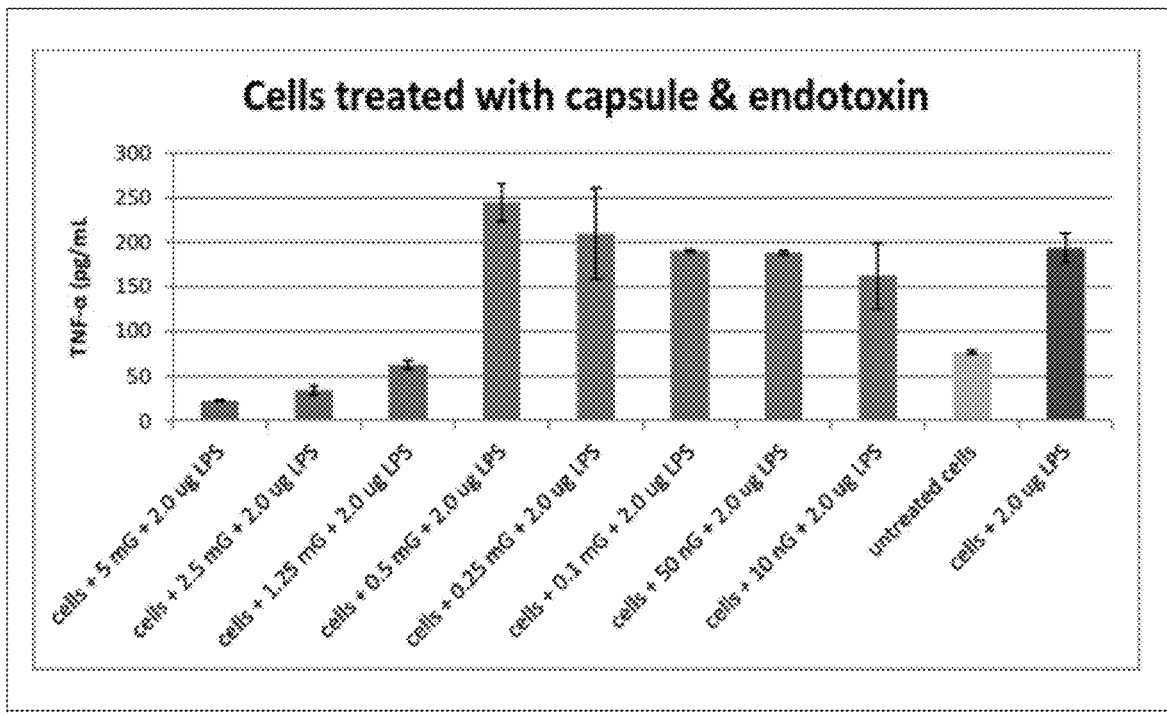
FIG. 4 shows the results of the anti-inflammatory effect of the low molecular weight porcine lympho-reticular polypeptides. The product shows a significant anti-inflammatory effect for 1.25-5.0 mg/mL. Concentrations below 1.25 mg/mL show no anti-inflammatory effect.

On the other hand, at concentrations of 5 mg/mL and below, the product showed downregulation of TNF-α at specific concentrations. The product downregulate the expression of TNF-α in cells activated with 2 ug of E. coli serotype 055:B5 endotoxin (LPS) at concentrations of 1.25-5.0 mg/mL. The downregulation is significant at p<0.05. These results suggest that the product acts as an ant inflammatory at concentrations ranging from 1.25-5.0 mg/mL. FIG. 4.

The product obtained through the method 1000 disclosed in the present invention does not compromise cell viability at concentrations of 5 mg/mL or below, but at the same time do display potential anti-inflammatory effects at concentrations of 1.25 mg/mL to 5 mg/mL, enables the possibility of using it as a therapeutically active agent at concentrations between 1.25 mg/mL to 5 mg/mL.

Since many modifications, variations and changes in detail can be made to the described embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for preparation of low molecular weight porcine lympho-reticular polypeptides, comprising:
   enzymatic hydrolysis of a source of protein, wherein the source of protein comprises a blend of porcine liver and porcine spleen, with an enzyme having proteolytic activity and an enzyme having amylase activity.

2. The method of claim 1, wherein the blend of porcine liver and spleen, is present at a ratio of about 2:8 to 8:2 respectively.

3. The method of claim 1, wherein the enzyme having proteolytic activity is selected from the group consisting of pancreatin, papain, pepsin, or mixtures thereof.

4. The method of claim 1, wherein the enzyme having amylase activity is diastase.

5. The method of claim 3, wherein the papain is used at an amount ranging from 0.5 to 2.0 ounces per eleven pounds of the blend of porcine liver and spleen.

6. The method of claim 3, wherein the pepsin is used at an amount ranging from 1.5 to 3.5 ounces per eleven pounds of porcine glands.

7. The method of claim 3, wherein the pepsin is provided in the form of anhydrous pepsin.

8. The method of claim 3, wherein the pancreatin is used at an amount ranging from 0.05 to 1.0 ounces per eleven pounds of fresh porcine glands.

9. The method of claim 4, wherein the diastase is used at an amount ranging from 0.1 to 1.5 ounces per eleven pounds of fresh porcine glands.

10. The method of claim 1, further comprising a cleansing step in an aqueous surfactant solution containing benzalkonium chloride.

11. The method of claim 1, wherein the enzymatic hydrolysis has a pH range of between 4.5 to 5.5.

12. The method of claim 1, wherein the pH range is maintained by using a weak organic acid.

13. The method of claim 12, where the weak organic acid is citric acid.

14. The method of claim 12, further comprising adding Methyl 4-hydroxybenzoate and Propyl 4-hydroxybenzoate.

15. The method of claim 1, carried out at a temperature of 35° C. and 55° C.

* * * * *